US009545374B1

(12) United States Patent
Sanders et al.

(10) Patent No.: US 9,545,374 B1
(45) **Date of Patent: *Jan. 17, 2017**

(54) METHOD, COMPOSITION FOR THE PREPARATION AND CLEANING OF PHOTO CHROMIC DYES RESULTING IN A PRODUCT SUITABLE FOR USE ON HUMAN SKIN

(71) Applicant: Sanders Research, Carrollton, TX (US)

(72) Inventors: Clifton Sanders, Carrollton, TX (US); Courtland Imel, Dallas, TX (US)

(73) Assignee: GENESIS LABORATORIES, INC., Carrollton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/145,410

(22) Filed: May 3, 2016

(51) Int. Cl.
*A61K 8/96* (2006.01)
*A61Q 17/04* (2006.01)
*C09K 9/00* (2006.01)

(52) U.S. Cl.
CPC ................. *A61K 8/96* (2013.01); *A61Q 17/04* (2013.01); *C09K 9/00* (2013.01)

(58) Field of Classification Search
CPC .............. A61K 8/96; A61Q 17/04; C09K 9/00
See application file for complete search history.

(56) References Cited

U.S. PATENT DOCUMENTS 5,628,934 A 5/1997 Ohno et al.
5,730,961 A 3/1998 Goudjil
5,762,913 A 6/1998 Tanaka et al.
6,461,594 B1 * 10/2002 Chaiken .................. A61K 8/19 424/59
6,470,891 B2 * 10/2002 Carroll .................. C09D 11/50 128/897
7,022,331 B2 4/2006 Theisen
7,776,316 B2 8/2010 Kolodziej et al.
2002/0192247 A1 * 12/2002 Theisen .................. A61K 8/63 424/401
2007/0183992 A1 8/2007 Dumousseaux et al.

FOREIGN PATENT DOCUMENTS

CN 104068486 A 10/2014
CN 104164151 A 11/2014
CN 104988766 A 10/2015

OTHER PUBLICATIONS

Deligeorgiev et al, Synthesis of photochromic chelating spironaphthoxazines, 2002, Dye and Pigments, 53, pp. 101-108.*

* cited by examiner

*Primary Examiner* — Trevor Love
(74) *Attorney, Agent, or Firm* — Robert C. Klinger

(57) ABSTRACT

A method and composition of a photo chromic dye suitable to be applied directly to human skin, and which dye is configured to indicate exposure to UV rays. The composition is configured to change color upon exposure to UVA, UVB and/or UVC rays. The composition can be used with other compositions, such as sunscreen, and be applied to human skin prior to application of the sunscreen, or, formulated with the sunscreen such that when the active ingredients of the sunscreen diminish, the photo chromic dye will change color to generate a visual indicator of this condition.

1 Claim, 1 Drawing Sheet

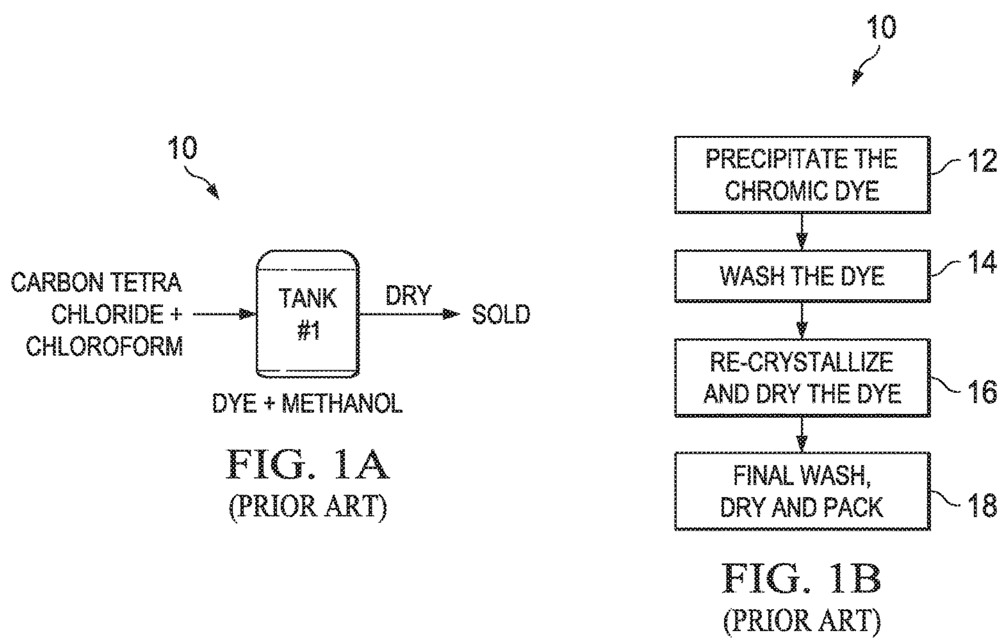
FIG. 1A
(PRIOR ART)
FIG. 1B
(PRIOR ART)
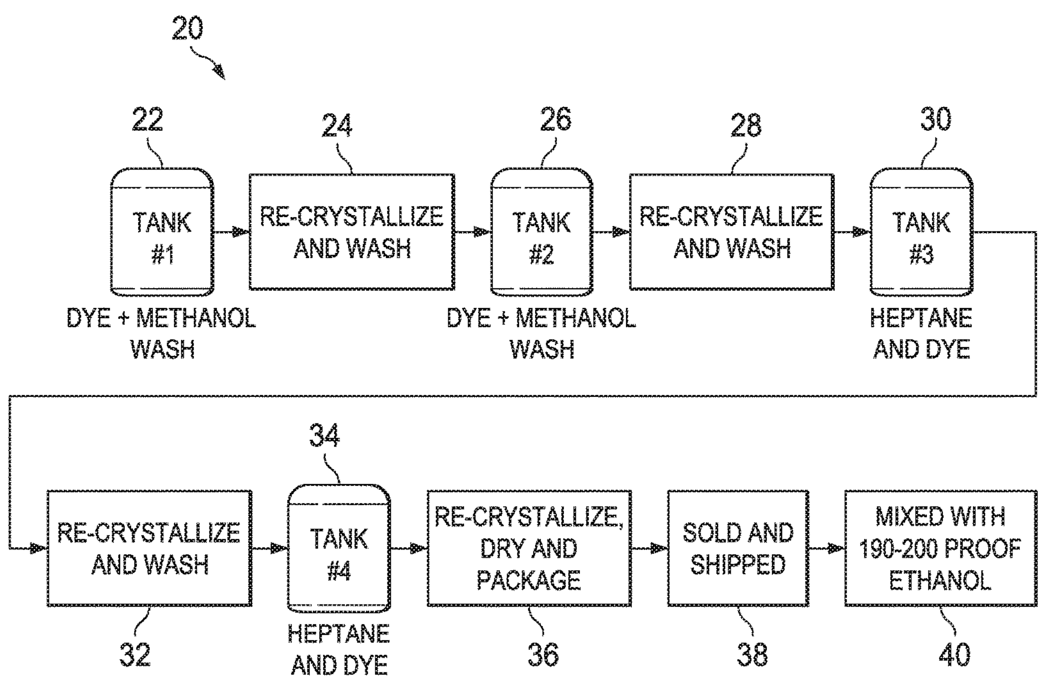
FIG. 2

METHOD, COMPOSITION FOR THE PREPARATION AND CLEANING OF PHOTO CHROMIC DYES RESULTING IN A PRODUCT SUITABLE FOR USE ON HUMAN SKIN

TECHNICAL FIELD

The present disclosure relates to new manufacturing processes that remove known carcinogens from producing photo chromic inks and dyes. This enables the materials to be applied to human skin without causing adverse reactions.

BACKGROUND

Over eighty percent of the population will experience some type of reaction to their skin as a result of being exposed to Ultra Violet (UV) rays, such as UVA, UVB, and UVC rays. Such skin damage is photochemical in nature and is directly associated with high energy, short wavelength radiation. The end result is an undesirable biological change, such as inflammation and mutations to the DNA.

The use of photo chromic dyes that illuminate between 200 nm and 600 nm serve as indicators to the public alerting them of their exposure to Ultra Violet rays.

The current manufacturing processes of photo chromic dyes result in residual amounts of carcinogens remaining in, and on, these materials. By re-defining the manufacturing process, we are able to remove these carcinogens without altering chemical structure or function of the dyes.

These manufacturing processes are common throughout the industry for those companies manufacturing photo chromic dyes. These photo chromic dyes were not originally intended to be applied to human skin. Subsequently, there was no need to remove the affected carcinogens because the inks were used in other mediums (i.e. plastics, paper, t-shirts, and other novelty items).

BRIEF SUMMARY

This disclosure provides a method and composition of a photo chromic dye suitable to be applied directly to human skin, and which dye is configured to indicate exposure to UV rays. The composition is configured to change color upon exposure to UVA, UVB and/or UVC rays. The composition can be used with other compositions, such as sunscreen, and be applied to human skin prior to application of the sunscreen, or, formulated with the sunscreen such that when the active ingredients of the sunscreen diminish, the chromic dye will change color to generate a visual indicator of this condition.

BRIEF DESCRIPTION OF THE DRAWINGS

FIG. 1A is an apparatus, and FIG. 1B is a conventional method for producing a chromic dye that includes carcinogens using the apparatus of FIG. 1A; and FIG. 2 is a diagram of a method for producing a non-toxic chromic dye without carcinogens, and which can be directly applied to human skin for detecting exposure to UVA, UVB, and UVC rays.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Conventional and toxic chromic dyes are commercially available from numerous sources, such as Pittsburgh Paint and Glass of Pittsburgh, Pa.

Conventional Cleaning Process for Photochromic Dyes

Referring to FIGS. 1A and 1B, there is shown a conventional manufacturing process at 10 for processing a chromic dye that is toxic and contains carcinogens. The conventional chromic dye is not suitable to be applied directly to human skin, but rather to, mediums such as plastics, paper, t-shirts, and other novelty items.

At step 12, the manufactured chromic dye is precipitated.

At step 14, the chromic dye is washed in a tank in an equal portion of Carbon Tetra Chloride and Chloroform.

At step 16, the chromic dye is re-crystallized and dried in a rotary dryer.

At step 18, the chromic dye crystals are washed in 100% methanol, dried and packed.

Cleaning Process for Chromic Dyes Suitable for Human Skin

Referring to FIG. 2, there is shown one exemplary embodiment of a manufacturing process at 20 for producing a photo chromic dye that is non-toxic and suitable for application to human skin, such as for use as a UVA, UVB and/or UVC indicator. The photo chromic dye is configured to illuminate at a wavelength of between 200 nm and 600 nm, although other wavelengths are possible.

At step 22, the step of washing the photo chromic dye in Carbon Tetra Chloride and Chloroform previously described in step 14 is removed entirely from the manufacturing process. The photo chromic dye is washed in a first tank a first time with an alcohol based solution, preferably a 100% methanol wash in one exemplary embodiment. Ethanol Propanol can be used in another exemplary embodiment. This step removes impurities that are harmful to human skin, such as toxins and carcinogens.

At step 24, the photo chromic dye is re-crystalized and dried.

At step 26, the re-crystalized and dried photo chromic dye is washed in a second tank a second time in an alcohol based solution, preferably a 100% methanol wash in one exemplary embodiment, and Ethanol Propanol in another exemplary embodiment. This additional wash is preferable, but not required if the wash of step 22 is sufficient to completely remove impurities that are harmful to human skin, such as toxins and carcinogens.

At step 28 the photo chromic dye is re-crystalized and dried again.

At step 30, the re-crystallized and dried photo chromic dye is then washed a first time in an acyclic aliphatic solution, preferably 100% heptanes. Acetone may be used in another exemplary embodiment. This wash in 100% heptanes is effective to completely remove impurities that are harmful to human skin, such as toxins and carcinogens.

At step 32 the photo chromic dye is re-crystalized and dried again.

At step 34, the re-crystallized and dried photo chromic dye is then washed a second time in an acyclic aliphatic solution, preferably 100% heptanes in one exemplary embodiment, and Acetone in another exemplary embodiment.

At step 36, the photo chromic dye is re-crystalized and dried. The resulting non-toxic photo chromic dye is then packaged for sale and shipment, as depicted in step 38.

At step 40, upon receipt of the packaged non-toxic photo chromic dye, and before formulation of the photo chromic dye in a carrier, the photo chromic dye is washed in 190-200 proof ethanol to ensure that there is no trace of heptanes in the photo chromic dye.

This process is safe, timely and cost effective.

In another exemplary embodiment, the photo chromic dye can be washed only once in an alcohol based solution, such as only once in methanol or Ethanol Propanol, and only once in an acyclic aliphatic solution, such as 100% heptanes or Acetone. However, performing each wash twice helps ensure the production of the non-toxic photo chromic dye suitable for application to human skin. In another exemplary embodiment, the photo chromic dye may be washed more than once in an alcohol based solution, and more than twice in an acyclic aliphatic solution, such as 100% heptanes.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A composition of manufactured photo chromic dye that is non-toxic to human skin and free of carcinogens, and is suitable for application to human skin, wherein the composition is made by a process that does not include any known carcinogens.

* * * * *